US011647751B2

(12) United States Patent
Alves Corrêa et al.

(10) Patent No.: US 11,647,751 B2
(45) Date of Patent: May 16, 2023

(54) USE OF PHOSPHORUS CONTAINING HERBICIDES AS DESICCANT FOR PLANTS OF THE GENUS *SACCHARUM*

(71) Applicant: BASF SE, Ludwigshafen am Rhein (DE)

(72) Inventors: Luis Eduardo Alves Corrêa, Sao Paolo (BR); Paulo Cesar Idalgo Donadoni, Sao Paolo (BR); Thiago De OLIVIERA, Sao Paolo (BR); Juliano Negrisido Della Valle, Sao Paolo (BR); Rodolfo Carvalho César De San Juan, Sao Paolo (BR)

(73) Assignee: BASF SE, Ludwigshafen (DE)

( * ) Notice: Subject to any disclaimer, the term of this patent is extended or adjusted under 35 U.S.C. 154(b) by 57 days.

(21) Appl. No.: 15/104,499

(22) PCT Filed: Dec. 16, 2014

(86) PCT No.: PCT/EP2014/077950
§ 371 (c)(1),
(2) Date: Jun. 14, 2016

(87) PCT Pub. No.: WO2015/091472
PCT Pub. Date: Jun. 25, 2015

(65) Prior Publication Data
US 2016/0316757 A1 Nov. 3, 2016

(30) Foreign Application Priority Data
Dec. 18, 2013 (EP) .................................. 13197931

(51) Int. Cl.
*A01N 57/20* (2006.01)
*A01N 43/66* (2006.01)
*C07H 1/08* (2006.01)

(52) U.S. Cl.
CPC ............. *A01N 57/20* (2013.01); *A01N 43/66* (2013.01); *C07H 1/08* (2013.01)

(58) Field of Classification Search
CPC ........... A01N 57/20; A01N 43/66; C07H 1/08
See application file for complete search history.

(56) References Cited

U.S. PATENT DOCUMENTS

| 3,988,142 A * | 10/1976 | Franz ................... C07F 9/4006 504/195 |
| 3,996,040 A * | 12/1976 | Franz ................... C07F 9/3808 504/203 |
| 5,258,358 A | 11/1993 | Kocur et al. |
| 5,491,125 A | 2/1996 | Albrecht et al. |
| 2005/0266995 A1 | 12/2005 | Frisch et al. |
| 2005/0266998 A1 | 12/2005 | Frisch et al. |
| 2005/0266999 A1 | 12/2005 | Frisch et al. |
| 2007/0184982 A1 | 8/2007 | Long |
| 2008/0045415 A1 | 2/2008 | Baur et al. |

FOREIGN PATENT DOCUMENTS

| CU | 23631 A1 | 2/2011 |
| DE | 32 00 486 A1 | 7/1983 |
| DE | 3200486 A * | 7/1983 |
| EP | 0 048 436 A1 | 3/1982 |
| EP | 0 336 151 A2 | 10/1989 |
| WO | 2008/059053 A1 | 5/2008 |
| WO | 2008/155097 A2 | 12/2008 |
| WO | 2010/105971 A2 | 9/2010 |

OTHER PUBLICATIONS

Snyman, Sandra, Evaluation of Transgenic Herbicide (Glufosinate Ammonium) Resistant Sugarcane (*Saccharum* Spp. Hybrids) Under Field Conditions, 2002, Plant Biotechnology 2002 and Beyond, I.K. Vasil (ed.), pp. 151-152.*
Leibbrandt, NB, Initial Field Testing of Transgenic Glufosinate Ammonium-Resistant Sugarcane, 2001, Proc S. African Sugarcane Technological Association, vol. 75, pp. 108-111.*
Burstell H. et al., DE3200486, Internet Translation for Reference N. Translation powered by EPO and Google, 1983. 5 pages. (Year: 1983).*
Bonnett, G., Chapter 3—Developmental Stages (Phenology), 2013, Sugarcane: Physiology, Biochemistry, and Functional Biology, pp. 35-53. (Year: 2013).*
Growth Stages of Mono-and Dicotyledonous Plants, BBCH Monograph, 2001, Federal Biological Research Centre for Agriculture and Forestry, 2nd Edition, 158 pages. (Year: 2001).*
Sison, C.M. et al., Control of Wild Sugarcane in Pineapple on the Del Monte Philippines, Inc. Plantation, 1993, Acta Horticulturae, 334, pp. 337-339. (Year: 1993).*
Carlos Alberto Mathias Azania et al., "The Use of Glyphosate in Surgarcane: A Brazilian Experience." Herbicides—Current Research and Case Studies in Use, Jun. 12, 2013, XP055108940.
Maria Gonnella et al., "Yield and quality of early potato cultivars in relation to the use glufosinate-ammonium as desiccant," Journal of the Science of Food and Agriculture, vol. 89, No. 5, Mar. 30, 2009, pp. 855-860, XP055109188.
Anonymous: "Pesticide Manual—Search," XP055109234.
International Search Report, dated Mar. 24, 2015, issued in PCT/EP2014/077950.
Gilda Brasil Camargo Cardoso, Piracicaba, 2011, Brazil.

(Continued)

*Primary Examiner* — Alton N Pryor
(74) *Attorney, Agent, or Firm* — Marshall, Gerstein & Borun LLP

(57) ABSTRACT

The invention primarily relates to the use of phosphorus containing herbicidal active ingredients (herbicides) as desiccant for (parts of) plants of the genus *Saccharum*, and to corresponding methods for desiccation, i.e. for the desiccating treatment. In another aspect the present invention relates to a method for increasing the amount of saccharose (sucrose) obtainable from (aerial parts of) plants of the genus *Saccharum officinarum*, and to a method for producing saccharose from (aerial parts of) plants of the genus *Saccharum officinarum*.

16 Claims, No Drawings

(56) References Cited

OTHER PUBLICATIONS

"Weed Management" Sugarcane. Netafim. (2012) pp. 1-2. http://www.sugarcanecrops.com/agronomic_practices/weed_management.

"Germination and Establishment Phase" Sugarcane. Netafim. (2012) p. 1. http://www.sugarcanecrops.com/crop_growth_phases/germination_establishment_phase/.

"The agronomic benefits of glyphosate in Europe—Review of the benefits of glyphosate per market use" Monsanto International Sarl, Monsanto Europe SA, Feb. 2010, pp. 1-82.

Batista, "Avaliação morfofisiológica da cana-de-açúcar sob diferentes regimes hídricos", Dissertação De Mestrado Em Agronomia, Mar. 2013, 125 pages.

Miguel, "Herbicidas dessecantes: momento de aplicação, eficiência e influência no rendimento e na qualidade de sementes de feijão", Tese de doutorado, Piracicaba: Universidade de São Paulo, May 2003, 123 pages.

* cited by examiner though a modern chopper harvester can complete the harvest faster and more efficiently than hand cutting and loading. Such mechanical harvesting doesn't require the field to be set on fire; the remains left in the field by the machine typically re the top of the sugar cane and the leaves.

USE OF PHOSPHORUS CONTAINING HERBICIDES AS DESICCANT FOR PLANTS OF THE GENUS *SACCHARUM*

CROSS REFERENCE TO RELATED APPLICATIONS

This application is a § 371 National Stage Application of PCT/EP2014/077950, filed 16 Dec. 2014, which claims priority to EP 13197931.2, filed 18 Dec. 2013.

BACKGROUND

Field of the Invention

The invention primarily relates to the use of phosphorus containing herbicidal active ingredients (herbicides) as desiccant for (parts of) plants of the genus *Saccharum*, and to corresponding methods for desiccation, i.e. for the desiccating treatment. In another aspect the present invention relates to a method for increasing the amount of saccharose (sucrose) obtainable from (aerial parts of) plants of the genus *Saccharum officinarum*, and to a method for producing saccharose from (aerial parts of) plants of the genus *Saccharum officinarum*.

Description of Related Art

Sugarcane, or sugar cane, belongs to the grass family (Poaceae). Sugarcane are species of tall perennial true grasses of the genus *Saccharum*. In particular *Saccharum officinarum* and its hybrids are grown for the production of sugar, ethanol and other industrial uses in tropical and subtropical regions around the world. Currently, Brazil is the largest producer of sugar cane in the world, other major producers are India, China, Thailand, Pakistan and Mexico.

*Saccharum officinarum* grows in clumps consisting of a number of strong unbranched stems. The stems vary in color, typically being green, pinkish or purple. They are jointed, nodes being present at the bases of the alternate leaves. The internodes contain a fibrous white pith immersed in sugary sap. The elongated, linear, green leaves have thick midribs and saw-toothed edges and grow to a length of about 30 to 60 cm and width of 5 cm. The terminal inflorescence is a panicle up to 60 cm long, a pinkish plume that is broadest at the base and tapering towards the top. The fruits are dry and each one contains a single seed. When sugar cane is harvested, harvesting typically occurs before the plant flowers, as the flowering process causes a reduction in sugar content.

*Saccharum officinarum* plants have stout jointed fibrous stalks that are rich in sugar, and can measure in their final growth height up to about 5 m tall. All sugar cane species interbreed, and the major commercial cultivars are complex hybrids.

The main product of sugarcane is sucrose, which accumulates in the stalk internodes. Sucrose, extracted and purified in specialized factories, is used as raw material in human food industries or is fermented to produce ethanol. The world demand for sugar is the primary driver of sugarcane agriculture. Cane accounts for 80% of sugar produced.

Although sugar canes produce seeds, modern stem cutting has become the most common reproduction method. Each cutting must contain at least one bud, and the cuttings are sometimes hand-planted. In some countries, billet planting is common. Billets harvested from a mechanical harvester are planted by a machine which opens and recloses the ground. Once planted, a stand can be harvested several times; after each harvest, the cane sends up new stalks, called ratoons. Successive harvests give decreasing yields, eventually justifying replanting. Two to ten harvests are usually made depending on the type of culture. In a country with a mechanical agriculture looking for a high production of large fields, sugar canes are generally replanted after two or three harvests to avoid a lowering in yields.

Sugar cane harvested by hand or mechanically. Typically, in hand harvesting, the field is first set on fire. The fire burns the plant's dry leaves without harming the stalks and roots. Harvesters then cut the cane just above ground-level using cane knives or machetes.

Mechanical harvesting uses a combine, or sugar cane harvester. The modern harvester machine cuts the cane at the base of the stalk, strips the leaves, chops the cane into consistent lengths and deposits it into a transporter following alongside. The harvester then blows the trash back onto the field. Harvested cane must be rapidly processed. Once cut, sugar cane begins to lose its sugar content, and damage to the cane during mechanical harvesting accelerates this decline. This decline is offset because a modern chopper harvester can complete the harvest faster and more efficiently than hand cutting and loading. Such mechanical harvesting doesn't require the field to be set on fire; the remains left in the field by the machine typically re the top of the sugar cane and the leaves.

WO 2010/105971 A2 relates to a method for the pesticidal treatment of crops which have a final growth height of at least 140 cm, comprising the treatment with an encapsulated pesticide at a growth height of the crop of up to 120 cm.

In the thesis "Aplicação de dessecante na cultura de cana-de-açucar (*Saccharum* spp.) para colheita mecanizada" of Gilda Brasil Camargo Cardoso effects of the herbicide Gramoxone® (paraquat), when applied as desiccant in pre-harvest, in the system of cut, shipment and transport of sugar cane was evaluated (Universidade de São Paolo, Escola Superior de Agricultura "Luiz de Queiroz", Piracicaba 2011, Brazil).

WO 2008/155097 A2 relates to a method of improving the growth of a plant comprising applying to a plant a composition comprising a product, which comprises microcapsules comprising a dispersed solid active ingredient.

WO 2008/059053 discloses a method for increasing the dry biomass of a plant by treating a plant with a pesticide, e.g. pyraclostrobin. A suitable plant mentioned therein is corn. The plants are treated in the growing stage BBCH 30 to 70.

DE 32 00 486 A1 discloses the use of phosphinotricine for increasing the yield in biomoass and/or the content of certain plant substances, e.g. for increasing the content of sucrose in sugar cane. Azania et al. report in "Herbicides—Current Research and Case Studies in Use", Edited by A. J. Price and J. A. Kelton, published by InTech, Jun. 12, 2013, Chapter 7, p. 153-173, on the experiences of the application of glyphosate in sugarcane in Brazil.

DD 94 280 A discloses the use of certain phosphorus containing herbicidal active ingredients for desiccation and defoliation of plants, inter alia mentioning cotton, potato, canola, sugar beet, and sugarcane.

The authors of J. Sci. Food. Agric. 2009, 89(5), 855-860 investigated the yield and quality of early potato cultivars in relation to the use of glufosinate-ammonium as desiccant.

Herbicidal formulations, for example comprising glufosinate salts such as glufosinate-ammonium, are well known in the art, for example, from EP 0048436, EP 0336151 A2, U.S. Pat. No. 5,258,358, U.S. Pat. No. 5,491,125, US 2005/0266995 A1, US 2005/0266998 A1, US 2005/266999 A1, US 2007/0184982 A1 or US 2008/0045415 A1.

Generally, there still is a need for effective compositions for treating plants of the genus *Saccharum*, in particular *Saccharum officinarum*, which not only exhibit a strong desiccating effect, i.e. dry (out) plants of the genus *Saccharum*, or parts thereof, but also one or more further beneficial effects, i.e. additionally reduce the environmental impact, e.g. by reducing waste, allow easier, e.g. less time-consuming, harvesting and/or post-harvest processing, and/or improve or increase the crop yield, in particular of sugar containing plant material and/or of sugar. Overall, such additional benefits reduce costs and/or inconveniences of production, transit, and storage.

SUMMARY

The invention accordingly primarily relates to the use of
- a phosphorus containing herbicidal active ingredient, or
- a mixture comprising two or more phosphorus containing herbicidal active ingredients, or
- a composition comprising one or more phosphorus containing herbicidal active ingredients, as desiccant for plants or parts of plants of the genus *Saccharum*,
and/or
for increasing the yield, in particular the proportion by weight, of sugar in (preferably aerial parts of) plants of the genus *Saccharum*.

DETAILED DESCRIPTION OF A PREFERRED EMBODIMENT

Thus, in the context of the present invention a single phosphorus containing herbicidal active ingredients, a mixture of two or more phosphorus containing herbicidal active ingredients, or compositions comprising one or more phosphorus containing herbicidal active ingredients, optionally comprising other herbicidal active ingredients, may be used.

Compositions (and/or concentrates for obtaining compositions) for use in the context of the present invention are described for example in EP 0336151 A2, U.S. Pat. No. 5,258,358, U.S. Pat. No. 5,491,125, US 2005/0266995 A1, US 2005/0266998 A1, US 2005/266999 A1, US 2007/0184982 A1 and US 2008/0045415 A1.

Preferably, the one or more phosphorus containing herbicidal active ingredients are used in the form of a composition comprising or consisting of
(a) one or more phosphorus containing herbicidal active ingredients,
(b) water,
(c) one or more organic solvents,
(d) one or more surfactants, preferably one or more nonionic, cationic, anionic and/or zwitterionic surfactants, and optionally one, two, three or more further constituents selected from the following groups (e) to (g),
(e) inorganic salts (preferably ammonium salts),
(f) further active crop protectant ingredients free of phosphorus,
(g) other formulation adjuvants.

Surprisingly it has now been found that phosphorus containing herbicidal active ingredients, in particular those described in more detail hereinafter, exhibit a strong desiccating, i.e. drying or drying out, effect on (preferably aerial parts of) plants of the genus *Saccharum*, in particular on the leaves thereof. Consequently, harvesting is facilitated and easier, less time-consuming post-harvest processing possible, e.g. for obtaining plant ingredients like sucrose (saccharose), e.g. due to the reduction of impurities and accompanying plant materials.

In particular, as a result of the application of one or more phosphorus containing herbicidal active ingredients to (preferably aerial parts of) plants of the genus *Saccharum*, in particular to (preferably leaves of) *Saccharum officinarum*, energy consumption, particularly fuel consumption, is significantly reduced, in particular during mechanized harvesting, and subsequent drying, and transportation of the harvested plants. As additional environmental benefit, inter alia the amount of unwanted and waste biomass is reduced.

Further, the phosphorus containing herbicidal active ingredients improve or increase of the yield, in particular of the sugar containing plant material of plants of the genus *Saccharum*, more specifically of sugar, especially of sucrose in *Saccharum officinarum*.

It was also found that the treatment of (preferably aerial parts of) plants of the genus *Saccharum* with (compositions comprising) the one or more phosphorus containing herbicidal active ingredients did not adversely affect re-growing of plants of the genus *Saccharum*.

Overall, the present invention allows an increase in harvesting and production efficiency.

A further aspect of the present invention relates to the use of (compositions comprising) one or more phosphorus containing herbicidal active ingredients, in particular of one or more herbicidal active ingredients of formula (I), (I-a) or (I-b), for increasing the yield of plant material of a plant of the genus *Saccharum*, in particular of *Saccharum officinarum*.

The present invention allows operational ease for the sugarcane harvester allows decrease in the amount of unwanted impurities (e.g. trash content) and consequently also increases the efficiency of the subsequent extraction of sugarcane juice. Also, the separation process of dried leaves (straws) is faster and the heating value of the straw for energy production becomes greater. Further, the efficiency of boilers is increased and maintenance costs associated with the equipment for steam generation are reduced. Pre-harvest application of the desiccant may also significantly increase the cleaning efficiency of all raw material delivered to sugarcane plants.

As used herein the phrase "increasing the yield" or "increase the yield", of a plant of the genus *Saccharum* relates to an increase in the yield or content of a product or ingredient of the plant by a measurable amount over the yield or content of the same product or ingredient of the plant produced under the same conditions, but without the application of the method or the use according to the present invention. It is preferred that the yield is increased by at least 0.5%, more preferred that the increase is 1% or more, even more preferred 2% or more, and yet more preferred 4% or more. Yield can be expressed in terms of an amount by weight or volume of a product of the plant, and preferably is expressed in terms of the total weight of the sugar containing aerial parts of the *Saccharum* plant, more preferably the proportion (percentage by weight) of sucrose in the aerial parts of the *Saccharum* plant, even more preferably the total amount by weight of sucrose obtainable from the aerial parts of the *Saccharum* plant. The sugar (especially sucrose) containing aerial parts of the *Saccharum* plant particularly preferably are the stems and stalks of the *Saccharum* plant.

Preferably, the present invention to the use of (a composition comprising) the one or more phosphorus containing herbicidal active ingredients as desiccant for (preferably aerial parts, particularly the leaves, of) plants of the genus *Saccharum officinarum*, and/or for increasing the proportion by weight of sucrose in (preferably aerial parts, particularly stems or stalks, of) plants of the genus *Saccharum officinarum* or hybrids thereof.

Preference is given in the context of the present invention to the use of (compositions comprising) one or more phosphorus containing herbicidal active ingredients of formula (I) or the salts thereof,

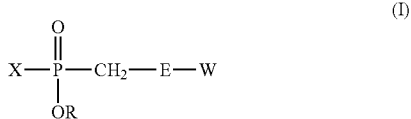
(I)

wherein

X is $C_1$-$C_4$ alkyl or OY, wherein Y is H, a cation, alkyl, alkenyl, alkoxyalkyl or unsubstituted or substituted $C_6$-$C_{10}$ aryl, R is H, alkyl or unsubstituted or substituted $C_6$-$C_{10}$ aryl, E is a structural element in total containing 1 to 22 carbon atoms linking W to the —$CH_2$—P(O)(OR)X moiety, preferably 1 to 18, more preferably 1 to 12, even more preferably 1 to 8 carbon atoms, and preferably 1 to 4 N-atoms, W is CN or $CO_2M$, wherein M is H or a cation.

In the context of the present invention further preference is given to the use of (compositions comprising) one or more phosphorus containing herbicidal active ingredients of formula (I-a) or the salts thereof,

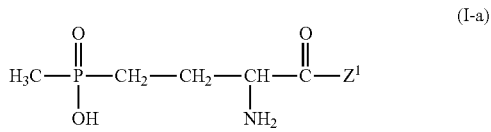
(I-a)

wherein $Z^1$ is a radical of the formula —OM, —NHCH($CH_3$)CONHCH($CH_3$)$CO_2$M or —NHCH($CH_3$)CONHCH[$CH_2$CH($CH_3$)$_2$]$CO_2$M, wherein M is H or a cation, and/or one or more phosphorus containing herbicidal active ingredients of formula (I-b) or the salts thereof,

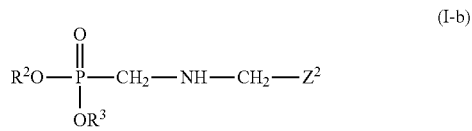
(I-b)

wherein $Z^2$ is a radical of the formula CN or $CO_2R_1$, in which $R^1$ is H, a cation, alkyl, alkenyl, alkoxyalkyl or unsubstituted or substituted $C_6$-$C_{10}$ aryl which is preferably unsubstituted or substituted by one or more radicals from the group consisting of alkyl, alkoxy, halogen, $CF_3$, $NO_2$ and CN, and $R^2$ and $R^3$ each independently of one another are H, a cation, alkyl or $C_6$-$C_{10}$ aryl which is unsubstituted or substituted, preferably unsubstituted or substituted by one or more radicals from the group consisting of alkyl, alkoxy, halogen, $CF_3$, $NO_2$ and CN, or biphenylyl.

Preferably, the carbon-containing radicals in connection with Q, $R^2$ or $R^3$, respectively, in total contain up to 10 carbon atoms, more preferably up to 6 carbon atoms.

Preferred compositions used in the context of the present invention comprise one or more phosphorus containing herbicidal active ingredients selected from the group consisting of glufosinate (salts), glyphosate (salts), and bilanafos (=bialaphos) (salts) [i.e. glufosinate and its salts, glyphosate and its salts, and bilanafos and its salts], more preferred is glufosinate and its salts. In case of salts being used, the cations (M in formulae (I), (I-a) and (I-b)) of said salts are preferably selected from the group consisting of $Na^+$, $K^+$, and ammonium $NH(R^4)_3^+$ wherein each $R^4$ independently is H or a $C_1$-$C_{12}$ alkyl group, preferably H or a $C_2$-$C_6$ alkyl group, more preferably $NH_4^+$ or a monoisopropylammonium group.

A particularly preferred phosphorus containing herbicidal active ingredient in the context of the present invention is glufosinate-ammonium.

The compounds of the formula (I-a) contain an asymmetric carbon atom. The L enantiomer is regarded as being the biologically active isomer. The formula (I-a) therefore embraces all stereoisomers and mixtures thereof, particularly the racemate, and the biologically active enantiomer in each case. Examples of active ingredients of the formula (I-a) are as follows:

glufosinate and its ammonium salt in racemic form, i.e., 2-amino-4-[hydroxy(methyl)phosphinoyl]butanoic acid and its ammonium salt, the L enantiomer of glufosinate and its ammonium salt, bilanafos=bialaphos, i.e., L-2-amino-4-[hydroxy(methyl)phosphinoyl]butanoyl-L-alaninyl-L-alanine and its sodium salt.

The racemate of glufosinate-ammonium on its own is usually applied at rates of between 200 and 1000 g a.i./ha (i.e., grams of active ingredient (a.i.) per hectare). Glufosinate-ammonium at these rates is effective in particular when it is taken up via green parts of the plant. Glufosinate-ammonium generally is used predominantly for controlling broadleaf and gramineous weeds in plantation crops and on uncultivated lands and also, using special application techniques, for inter-row control in agricultural or surface crops.

The compounds of the formula (I-b) comprise N-(phosphonoalkyl)glycine and hence derivatives of the amino acid glycine. The herbicidal derivatives of N-(phosphonomethyl)glycine (glyphosate) have been described, for example, in U.S. Pat. No. 3,799,758.

Generally speaking, glyphosate is used in crop protectant formulations in the form of the water-soluble salts, with the isopropylammonium salt being of particular significance in connection with the present invention.

For the purpose of the present invention, foliar application of (compositions comprising) one or more phosphorus containing herbicidal active ingredients, in particular of one or more herbicidal active ingredients of formula (I), (I-a) or (I-b), to the *Saccharum* plant is preferred. In a preferred embodiment, said foliar application is carried out via aerial application (e.g. using an aeroplane). In contrast thereto, ground application is not preferred.

In a particularly preferred embodiment, the present invention relates to the use or the method according to the present invention, wherein glufosinate-ammonium, or
a mixture comprising glufosinate-ammonium and a further phosphorus containing herbicidal active ingredients, or
a composition comprising glufosinate-ammonium and optionally one or more further phosphorus containing herbicidal active ingredients,
is used as desiccant for plants of the genus *Saccharum*, preferably as desiccant for (preferably aerial parts, particularly the leaves, of) plants of the genus *Saccharum officinarum*, in particular sugarcane.

In an even more preferred embodiment, the present invention relates to the use or the method according to the present invention, wherein
glufosinate-ammonium, or
a composition comprising glufosinate-ammonium and optionally one or more further phosphorus containing herbicidal active ingredients,
is used as desiccant for aerial parts, particularly the leaves, of plants of the genus *Saccharum officinarum*, in particular sugarcane.

For the purpose of the present invention, preferably (compositions comprising) one or more phosphorus containing herbicidal active ingredients, in particular one or more herbicidal active ingredients of formula (I), (I-a) or (I-b), are applied in a total amount in the range of from 100 to 1500 g/ha, more preferably in the range of from 150 to 1250 g/ha, even more preferably in the range of from 250 to 1000 g/ha to the plants of the genus *Saccharum*.

In an even more preferred embodiment, the present invention relates to the use or the method according to the present invention, wherein
glufosinate-ammonium, or
a composition comprising glufosinate-ammonium
is used as desiccant for aerial parts, particularly the leaves, of sugarcane plants,
wherein preferably glufosinate-ammonium is applied in a total amount in the range of from 150 to 1250 g/ha, even more preferably in the range of from 250 to 1000 g/ha to the sugarcane plants.

In the context of the present invention, an use or a method of the present invention may be carried only once or two, three, four, five, six, seven, or eight times or more per full life cycle of a plant of the genus *Saccharum*.

Preferably, an use or a method of the present invention is carried only once or twice per full life cycle of a plant of the genus *Saccharum*, typically once per season.

The use or method according to the present invention is preferably performed such that one or more treatments with (a composition comprising) the one or more phosphorus containing herbicidal active ingredients, in particular one or more herbicidal active ingredients of formula (I), (I-a) or (I-b), are carried out 3 to 30 days, preferably 4 to 24 days, more preferably 5 to 18 days before harvesting.

The use or method according to the present invention is preferably performed such that the last treatment with (a composition comprising) the one or more phosphorus containing herbicidal active ingredients, in particular one or more herbicidal active ingredients of formula (I), (I-a) or (I-b), is carried out 3 to 30 days, preferably 4 to 24 days, more preferably 5 to 18 days before harvesting.

Thus, harvesting, preferably mechanical harvesting, is preferably carried out 3 to 30 days, more preferably 4 to 24 days, yet more preferably 5 to 18 days after the last application of phosphorus containing herbicidal active ingredients.

In a preferred embodiment of the present invention, (compositions comprising) the one or more phosphorus containing herbicidal active ingredients, in particular one or more herbicidal active ingredients of formula (I), (I-a) or (I-b), are used which are free of an effective amount of encapsulated pesticide as described in WO 2010/105971 A2 and/or free of an effective amount of core-shell microcapsules as described in WO 2008/155097 A2.

In a preferred embodiment of the present invention, (compositions comprising) the one or more phosphorus containing herbicidal active ingredients, in particular one or more herbicidal active ingredients of formula (I), (I-a) or (I-b), are used which are free of an effective amount of encapsulated pesticide and/or free of an effective amount of core-shell microcapsules, more preferably free of encapsulated pesticides and/or free of core-shell microcapsules, even more preferred free of capsules and free of microcapsules.

In a preferred embodiment of the present invention, (compositions comprising) the one or more phosphorus containing herbicidal active ingredients, in particular one or more herbicidal active ingredients of formula (I), (I-a) or (I-b), are used in absence of, i.e. without a further active crop protectant ingredient free of phosphorus (constituent (f) of compositions for use according to the present invention).

In a preferred embodiment, plants of the genus *Saccharum*, in particular of *Saccharum officinarum*, are treated in accordance with the present invention when having reached a total height (measured from the ground) of 150 cm or taller, preferably of 200 cm or taller, more preferably of 250 cm or taller, even more preferably of 300 cm or taller.

The term "growth stage" refers to the growth stages as defined by the BBCH Codes in "Growth stages of mono- and dicotyledonous plants", 2nd edition 2001, edited by Uwe Meier from the Federal Biological Research Centre for Agriculture and Forestry. The BBCH codes are a well-established system for a uniform coding of phenologically similar growth stages of all mono- and dicotyledonous plant species. Some of these BBCH growth stages are indicated in the following.

Growth stage 3: Stem elongation, shoot development (main shoot)
BBCH 31—Stem 10% of final length; 1 node detectable
BBCH 33—Stem 30% of final length; 3 nodes detectable
BBCH 36—Stem 60% of final length; 6 nodes detectable
BBCH 39—Maximum stem length reached; 9 or more nodes detectable Growth stage 4: Development of harvestable vegetative plant parts (main shoot)
BBCH 40—Harvestable vegetative plant parts begin to develop
BBCH 45—Harvestable vegetative plant parts have reached 50% of final size
BBCH 49—Harvestable vegetative plant parts have reached final size Growth stage 5: Inflorescence emergence (main shoot)/heading
BBCH 51—Inflorescence or flower buds visible
BBCH 55—First individual flowers visible (still closed)

Growth stage 6: Flowering (main shoot)
BBCH 60—First flowers open (sporadically)
BBCH 64—40% of flowers open
BBCH 69—End of flowering: fruit set visible In another preferred embodiment plants of the genus *Saccharum* are treated in accordance with the present invention at a growth stage later than BBCH 31 (stem 10% of final length), preferably later than BBCH 35 (stem 50% of final length), more preferably later than BBCH 37 (stem 70% of final length).

Preferably, plants of the genus *Saccharum* are treated in accordance with the present invention at a growth stage of BBCH 38 (stem 80% of final length) to BBCH 85 (advanced ripening or fruit colouration), more preferably at growth stage BBCH 39 (stem 90% of final length) to BBCH 79 (nearly all fruits have reached final size), even more preferably at growth stage BBCH 40 (harvestable vegetative plant parts begin to develop) to BBCH 71 (10% of fruits have reached final size).

Particularly preferably, plants of the genus *Saccharum* are treated in accordance with the present invention at a growth stage of BBCH 43 (harvestable vegetative plant parts have reached 30% of final size) to BBCH 69 (end of flowering: fruit set visible), yet more preferably at a growth stage of BBCH 47 (harvestable vegetative plant parts have reached 70% of final size) to BBCH 65 (50% of flowers open).

In another preferred embodiment, plants of the genus *Saccharum* are treated in accordance with the present invention at a growth stage later than BBCH 49 (harvestable vegetative plant parts have reached final size).

In connection with the present invention the term "organic solvents" (constituent (c) of a composition for use in accordance with the present invention) includes, for example, nonpolar organic solvents, polar protic organic solvents or aprotic organic polar solvents and mixtures thereof. Examples of organic solvents in the sense of the invention are
- aliphatic or aromatic hydrocarbons, such as mineral oils and toluene, xylenes and naphthalene derivatives, for example,
- halogenated aliphatic or aromatic hydrocarbons such as methylene chloride and chlorobenzene;
- aliphatic alcohols, such as alkanols having 1 to 12 carbon atoms, preferably 1 to 6 carbon atoms, such as methanol, ethanol, propanol, isopropanol and butanol, for example, or polyhydric alcohols such as ethylene glycol, propylene glycol and glycerol;
- ethers such as diethyl ether, tetrahydrofuran (THF), and dioxane;
- alkylene glycol monoalkyl and dialkyl ethers, such as propylene glycol monomethyl ether, propylene glycol monoethyl ether, ethylene glycol monomethyl and monoethyl ether, diglyme, and tetraglyme, for example;
- amides such as dimethylformamide (DMF), dimethylacetamide, dimethylcaprylamide, dimethylcapramide (®Hallcomide), and N-alkylpyrrolidones;
- ketones such as acetone;
- esters based on glyceryl and carboxylic acids, such as glyceryl mono-, di- and triacetate,
- phthalic esters;
- lactams;
- carbonic diesters;
- nitriles such as acetonitrile, propionitrile, butyronitrile, and benzonitrile;
- sulfoxides and sulfones such as dimethyl sulfoxide (DMSO) and sulfolane;
- oils, examples being plant-based oils such as corn germ oil, rapeseed oil or soybean oil.

In many cases combinations of two or more different solvents, such as combinations containing alcohols such as methanol, ethanol, n- and isopropanol, and n-, iso-, tert- and 2-butanol, are also suitable.

Preferred organic solvents in the sense of the present invention are aromatic solvents such as toluene, o-, m- or p-xylene and mixtures thereof, 1-methylnaphthalene, 2-methylnaphthalene, $C_6$-$C_{16}$ aromatics mixtures such as, for example, the Solvesso® series (ESSO) with the grades Solvesso® 100 (b.p. 162-177° C.), Solvesso® 150 (b.p. 187-207° C.), and Solvesso® 200 (b.p. 219-282° C.), phthalic acid ($C_1$-$C_{12}$)alkyl esters, especially phthalic acid ($C_4$-$C_8$) alkyl esters, water-immiscible ketones, such as cyclohexanone or isophorone, for example, or $C_6$-$C_{20}$ aliphatics, which may be linear or cyclic, such as the products of the Shellsol® series, grades T and K, or BP-n paraffins, and esters such as glyceryl triacetate.

Particular preference is given to polar organic solvents, preferably polar organic solvents of substantial or unlimited miscibility with water which are suitable for preparing an single-phase aqueous solution. These preferably are selected from the group consisting of N-methylpyrrolidone (NMP), propylene glycol monomethyl ether (e.g. Dowanol® PM), dimethylformamide (DMF), dimethylacetamide (DMA), THF (tetrahydrofuran), propylene glycol, dipropylene glycol, glycerol, iso-propanol, and tetrahydrofurfuryl alcohol.

The compositions for use according to the present invention preferably comprise surfactants (surface-active compounds) as constituent (d), preferably one or more anionic, cationic or zwitterionic and/or nonionic surfactants. The surfactants contribute to improved stability, availability of the one or more phosphorus containing herbicidal active ingredients for the *Saccharum* plants, or activity of the phosphorus containing herbicidal active ingredients, preferably those corresponding to formulae (I), (I-a) and (I-b).

Preferably, a composition for use in accordance with the present invention comprises one or more anionic surfactants, preferably one or more anionic surfactants and one or more nonionic surfactants.

Examples of suitable anionic surfactants are (where EO=ethylene oxide units, PO=propylene oxide units and BO=butylene oxide units):
- d1-1) anionic derivatives of fatty alcohols having 10-24 carbon atoms with 0-60 EO and/or 0-20 PO and/or 0-15 BO in any order, in the form of ether carboxylates, sulfonates, sulfates, and phosphates, and their inorganic salts (e.g., alkali metal and alkaline earth metal salts) and organic salts (e.g., salts based on amine or alkanolamine), such as Genapol®LRO, Sandopan® grades, and Hostaphat/Hordaphos® grades from Clariant;
- d1-2) anionic derivatives of copolymers consisting of EO, PO and/or BO units having a molecular weight of 400 to $10^8$, in the form of ether carboxylates, sulfonates, sulfates, and phosphates, and their inorganic salts (e.g., alkali metal and alkaline earth metal salts) and organic salts (e.g., salts based on amine or alkanolamine),
- d1-3) anionic derivatives of alkylene oxide adducts of $C_1$-$C_9$ alcohols, in the form of ether carboxylates, sulfonates, sulfates and phosphates, and their inorganic salts (e.g., alkali metal and alkaline earth metal salts) and organic salts (e.g., salts based on amine or alkanolamine);
- d1-4) anionic derivatives of fatty acid alkoxylates, in the form of ether carboxylates, sulfonates, sulfates and phosphates, and their inorganic salts (e.g., alkali metal and alkaline earth metal salts) and organic salts (e.g., salts based on amine or alkanolamine).

Preferred anionic surfactants are
  alkyl polyglycol ether sulfates, especially fatty alcohol diethylene glycol ether sulfate (e.g., Genapol LRO®, Clariant), or
  alkyl polyglycol ether carboxylates (e.g., 2-(isotridecyloxypolyethyleneoxy)ethyl carboxymethyl ether, Marlowet 4538®, Hüls).

Examples of cationic or zwitterionic surfactants are as follows (where EO=ethylene oxide units, PO=propylene oxide units, and BO=butylene oxide units):
  d2-1) alkylene oxide adducts of fatty amines, quaternary ammonium compounds having 8 to 22 carbon atoms ($C_8$-$C_{22}$), such as the Genamin® C, L, O, and T grades from Clariant, for example;
  d2-2) surface-active zwitterionic compounds such as taurides, betaines and sulfobetaines in the form of Tegotain® grades from Goldschmidt, and Hostapon®T and Arkopon®T grades from Clariant.

Examples of nonionic surfactants are:
  d3-1) fatty alcohols having 10-24 carbon atoms with 0-60 EO and/or 0-20 PO and/or 0-15 BO in any order. Examples of such compounds are Genapol® C, L, O, T, UD, UDD, and X grades from Clariant, Plurafac® and Lutensol® A, AT, ON, and TO grades from BASF, Marlipal® 24 and O13 grades from Condea, Dehypon® grades from Henkel, and Ethylan® grades from Akzo-Nobel, such as Ethylan CD 120;
  d3-2) fatty acid alkoxylates and triglyceride alkoxylates such as the Serdox®NOG grades from Condea or the Emulsogen® grades from Clariant;
  d3-3) fatty acid amide alkoxylates such as the Comperlan® grades from Henkel or the Amam® grades from Rhodia;
  d3-4) alkylene oxide adducts of alkynediols, such as the Surfynol® grades from Air Products; sugar derivatives such as amino sugars and amido sugars from Clariant,
  d3-5) glucitols from Clariant,
  d3-6) silicone- and/or silane-based surface-active compounds such as the Tegopren® grades from Goldschmidt and the SE® grades from Wacker, and also the Bevaloid®, Rhodorsil®, and Silcolapse® grades from Rhodia (Dow Corning, Reliance, GE, Bayer),
  d3-7) surface-active sulfonamides, from Bayer, for example;
  d3-8) surface-active polyacrylic and polymethacrylic derivatives such as the Sokalan® grades from BASF;
  d3-9) surface-active polyamides such as modified gelatins or derivatized polyaspartic acid from Bayer, and derivatives thereof,
  d3-10) surfactant polyvinyl compounds such as modified PVP, such as the Luviskol® grades from BASF and the Agrimer® grades from ISP, or the derivatized polyvinyl acetates, such as the Mowilith® grades from Clariant, or the polyvinyl butyrates, such as the Lutonal® grades from BASF, the Vinnapas® and the Pioloform® grades from Wacker, or modified polyvinyl alcohols, such as the Mowiol® grades from Clariant,
  d3-11) surface-active polymers based on maleic anhydride and/or reaction products of maleic anhydride and also maleic anhydride copolymers and/or copolymers containing reaction products of maleic anhydride, such as the Agrimer® VEMA grades from ISP,
  d3-12) surface-active derivatives of montan waxes, polyethylene waxes, and polypropylene waxes, such as the Hoechst® waxes or the Licowet® grades from Clariant,
  d3-13) polyol-based alkylene oxide adducts, such as Polyglycol® grades from Clariant;
  d3-14) surface-active polyglycerides and derivatives thereof from Clariant.

The weight ratio of the total amount of phosphorus containing herbicidal active ingredients of constituent (a) to the total amount of anionic surfactants of constituent (d) in a composition for use in accordance with the present invention preferably is in the range from 5:1 to 1:10, preferably 5:1 to 1:10, in particular 2:1 to 1:6.

The weight ratio of the total amount of phosphorus containing herbicidal active ingredients of constituent (a) to the total amount of nonionic surfactants of constituent (d) in a composition for use in accordance with the present invention preferably is in the range from 20:1 to 1:1, preferably 10:1 to 2:1, especially 8:1 to 3:1.

The compositions for use according to the present invention preferably comprise, as part of constituent (d), one or more nonionic surfactants from the group of the alkylpolyglycosides. Preferred alkylpolyglycosides in this context are the following:
  alkylpolysaccharides and mixtures thereof such as those, for example, from the ®Atplus range from Uniqema, preferably Atplus 435,
  alkylpolyglycosides in the form of the APG® grades from Henkel, an example being ®Plantaren APG 225 (fatty alcohol $C_8$-$C_{10}$ glucoside),
  sorbitan esters in the form of the Span® or Tween® grades from Uniqema,
  cyclodextrin esters or ethers from Wacker,
  surface-active cellulose derivatives and algin, pectin, and guar derivatives such as the Tylose® grades from Clariant, the Manutex® grades from Kelco, and guar derivatives from Cesalpina,
  alkylpolyglycoside-alkylpolysaccharide mixtures based on $C_8$-$C_{10}$ fatty alcohol, such as ®Glucopon 225 DK and ®Glucopon 215 CSUP (Cognis).

Preferred as alkylpolyglycosides are the alkylpolyglycosides-alkylpolysaccharide mixtures such as Atplus 435.

The compositions for use according to the present invention may comprise as constituent (e) inorganic salts from the group of ammonium salts, examples being ammonium sulfate, ammonium chloride, ammonium bromide, preferably ammonium sulfate.

The use of alkylpolyglycosides as surfactants in crop protectant compositions is known in principle (see, for example U.S. Pat. No. 5,258,358). It is also mentioned therein that ammonium sulfate can be added as a frost protectant.

The compositions for use in the context of the present invention may optionally comprise as constituent (g) customary formulation adjuvants, for example stickers, wetters, dispersants, penetrants, preservatives, frost protectants, fillers, carriers, colorants, evaporation inhibitors, pH modifiers (such as buffers, acids, and bases), viscosity modifiers (e.g. thickeners) or defoamers (defoaming agents).

Preferred formulation adjuvants (g) are defoamers, frost protectants, carriers, evaporation inhibitors and preservatives, e.g., Mergal K9N® (Riedel) or Cobate C®.

In a preferred embodiment fatty acid mono-alkyl esters are used as a formulation adjuvant of constituent (g), preferably fatty acid mono-alkyl esters derived from vegetable oil, more preferably soybean oil methyl esters.

In the aqueous compositions for use in the context of the present invention it is often advantageous to add defoamers. Suitable defoamers include all customary defoamers, preferably silicone-based defoamers, such as silicone oils.

Preferred defoamers are those from the group of linear polydimethylsiloxanes having an average dynamic viscosity, measured at 25° C., in the range from 1000 to 8000 mPas (mPas=millipascal-second), preferably 1200 to 6000 mPas, and containing silica. Silica comprehends forms/modifications such as polysilicic acids, meta-silicic acid, ortho-silicic acid, silica gel, silicic acid gels, kieselguhr, precipitated $SiO_2$, etc.

Defoamers from the group of linear polydimethylsiloxanes contain as their chemical backbone a compound of the formula $HO—[Si(CH_3)_2—O—]_n—H$, in which the end groups are modified, by etherification for example, or, in general, are attached to the groups $—Si(CH_3)_3$.

Examples of defoamers of this kind are ®Rhodorsil Antifoam 416 (Rhodia) and ®Rhodorsil Antifoam 481 (Rhodia). ®Rhodorsil Antifoam 416 is a medium-viscosity silicone oil having a dynamic viscosity at 25° C. of about 1500 mPas and containing surfactant and silica. Because of the surfactant content the density is reduced as compared with the unadditized silicone oil, and amounts to about 0.995 g/cm³. ®Rhodorsil Antifoam 481 is a medium-viscosity silicone oil having a dynamic viscosity at 25° C. of about 4500 mPas and containing silica. The density amounts to about 1.045 g/cm³. Other defoamers from the silicone group are Rhodorsil 1824, Antimussol 4459-2 (Clariant), Defoamer V 4459 (Clariant), SE Visk and AS EM SE 39 (Wacker). The silicone oils can also be used in the form of emulsions.

The compositions used in the context of the present invention may additionally comprise (as constituent (f)) further active crop protectant ingredients, preferably herbicides from the group of diphenyl ethers, carbamates, thiocarbamates, triphenyltin and tributyltin compounds, haloacetanilides, herbicides from the group of diphenyl ethers, carbamates, thiocarbamates, triphenyltin and tributyltin compounds, haloacetanilides, phenoxyphenoxyalkanecarboxylic acid derivatives and heteroaryloxyphenoxyalkanecarboxylic acid derivatives, such as quinolyloxy-, quinoxalyloxy-, pyridyloxy-, benzoxalyloxy- and benzothiazolyloxyphenoxyalkanecarboxylic esters, which generally have a suitable solubility in organic solvents, examples being active ingredients such as oxyfluorfen, diclofop-methyl, fenoxaprop-ethyl or fenoxaprop-P-ethyl.

It is also possible to include one or more further active ingredients from the group of safeners, plant growth regulators, insecticides, and fungicides as constituent (f).

The compositions for use in the context of the present invention can be prepared by processes which are customary and known in the art, i.e., by mixing the ingredients with stirring or shaking or by means of static mixing techniques.

In the following examples, amounts are by weight, unless indicated otherwise.

The composition examples shown in the following table are concentrates suitable—after appropriate dilution with water—for use in the context of the present invention. The section "Biological examples" summarizes results of biological trials.

|  | 1 | 2 | 3 | 4 | 5 |
|---|---|---|---|---|---|
| Glufosinate-ammonium (a.i.) | 25.00 | 20.00 | 25.00 | 25.00 | 18.00 |
| $C_{12}/C_{14}$—O—$(EO)_2$—$SO_3^-Na^{+(2)}$ | 35.00 | 35.00 | 35.00 |  |  |
| Glucopon 225 DK$^{(3)}$ |  |  |  | 35.00 |  |
| Glucopon 215 CSUP$^{(3)}$ |  |  |  |  | 30.00 |
| Atplus 435$^{(3)}$ | 5.00 | 5.00 | 5.00 | 5.00 | 5.00 |
| Ammonium sulfate | 7.00 |  | 5.00 | 7.00 |  |
| Propylene glycol monomethyl ether | 3.00 |  | 3.00 |  |  |
| Propylene glycol |  | 2.75 |  | 2.50 | 2.50 |
| Rhodorsil 481$^{(4)}$ | 0.25 |  |  |  |  |
| Rhodorsil 416$^{(5)}$ |  | 0.25 |  |  |  |
| Antimussol 4459-2$^{(6)}$ |  |  | 0.50 |  |  |
| Rhodorsil 454$^{(7)}$ |  |  |  | 0.50 |  |
| Water | ad 100 | ad 100 | ad 100 | ad 100 | ad 100 |

Abbreviations used:
$^{(2)}C_{12}/C_{14}$—O—$(EO)_2$—$SO_3^-Na^+$ = $C_{12}/C_{14}$ fatty alcohol diethylene glycol ether sulfate (used as ® Genapol LRO, Clariant), ® TEGO XP 5902 = blend of trisiloxane and a sodium salt solution (Degussa) ® Empilan KAS = ethoxylated alcohol with 5 EO (Huntsman); ® Sapogenat T 300 = triisobutylphenol ethoxylate with 30 EO (Clariant), ® Berol 900 = alkylglyceride (castor ethoxylate) with 40 EO (Akzo-Nobel), ® Geropon-CF 812-I = sulfosuccinate amine salt (Rhodia)
$^{(3)}$® Glucopon 225 DK = alkylpolyglycoside-alkylpolysaccharide mixture based on $C_8$-$C_{10}$ fatty alcohol (Cognis), ® Glucopon 215 CSUP = alkylpolyglycoside-alkylpolysaccharide mixture based on $C_8$-$C_{10}$ fatty alcohol (Cognis), ® Atplus 435 = alkylpolyglycoside-alkylpolysaccharide mixture (Uniqema)
$^{(4)}$® Rhodorsil 481 = polydimethylsiloxane oil with silica gel (Rhodia)
$^{(5)}$® Rhodorsil 416 = polydimethylsiloxane oil with silica gel and surfactant (Rhodia)
$^{(6)}$® Antimussol 4459-2 = silicone-based defoamer emulsion (Clariant)
$^{(7)}$® Rhodorsil 454 = defoamer based on polydimethylsiloxane oil without silica (Rhodia)

The compositions disclosed in the above table are concentrates which are diluted with an appropriate amount of water, optionally adding further adjuvants like ammonium sulfate, thereby obtaining a tank mix. The thus obtained tank mix is preferably used such a total amount of herbicides of component (a) is applied to the *Saccharum* plants as indicated hereinbefore at growth stage as indicated hereinbefore.

Biological Examples

The compositions described in the table above were diluted with water and applied to a field of *Saccharum officinarum* plants at growth stage BBCH 49 (approximately 300 cm growth height; corresponding to about 2 weeks before harvest), such that the amount of glufosinate ammonium was 800 g/ha or 1000 g/ha, respectively. The evaluation 2 weeks after application of glufosinate ammonium revealed a desiccation of sugarcane leaves of 54% and 60%, respectively.

The invention claimed is:

1. A method for desiccating treatment of one or more plants of the genus *Saccharum*, comprising treatment of applying to said plants an effective amount of
   a composition comprising a phosphorus containing herbicidal active ingredient selected from the group consisting of glufosinate and salts thereof,
   to thereby have a drying out effect on the plant, wherein the treatment of the plants of the genus *Saccharum* is done at a growth height of 200 cm or more,
wherein the plants are selected from the group consisting of *Saccharum officinarum* and of hybrids of *Saccharum officinarum*,
wherein at least 54% of the leaves of the plants are desiccated,
wherein the treatment is carried out at a growth stage of later than BBCH 35,
and wherein the phosphorus containing herbicidal active ingredient is applied in a total amount in a range of from 800 to 1000 g/ha.

2. The method according to claim 1, wherein the phosphorus containing herbicidal active ingredient is glufosinate-ammonium.

3. The method according to claim 1, wherein the treatment is a foliar application.

4. The method according to claim 1, wherein a total amount of sucrose obtainable from a plant of the genus *Saccharum officinarum* and/or hybrids thereof is increased.

5. A method according to claim 1, comprising after the treatment (i):
 (ii) harvesting sucrose containing plant material comprising or consisting essentially of stalks,
 (iii) obtaining sucrose from the plant material resulting from (ii).

6. The method according to claim 5, wherein
 (ii) the harvesting is carried out 3 to 30 days after completion of (i), and/or
 (ii) the harvesting is carried out mechanically.

7. A method according to claim 1, wherein the treatment is carried out at a growth stage of later than BBCH 37.

8. A method according to claim 5, wherein the treatment is carried out at a growth stage of later than BBCH 37.

9. The method according to claim 1, wherein the treatment of the one or more plants of the genus *Saccharum* is performed at a growth height of 250 cm or more.

10. The method according to claim 1, wherein the treatment of the one or more plants of the genus *Saccharum* is performed at a growth height of 300 cm or more.

11. A method according to claim 1, wherein the treatment is carried out at a growth stage of BBCH 38 to BBCH 85.

12. A method according to claim 1, wherein the treatment is carried out at a growth stage of BBCH 40 to BBCH 71.

13. A method for desiccating treatment of one or more plants of the genus *Saccharum*, comprising treatment of applying to said plants an effective amount of
 a composition comprising a phosphorus containing herbicidal active ingredient selected from the group consisting of glufosinate and salts thereof,
 to thereby have a drying out effect on the plant,
 wherein the treatment of the plants of the genus *Saccharum* is done at a growth height of 250 cm or more,
 wherein the plants are selected from the group consisting of *Saccharum officinarum* and of hybrids of *Saccharum officinarum*,
 wherein the leaves of the plants are desiccated,
 wherein the treatment is carried out at a growth stage of later than BBCH 45,
 and wherein the phosphorus containing herbicidal active ingredient is applied in a total amount in a range of from 800 to 1000 g/ha.

14. The method according to claim 13, wherein the phosphorus containing herbicidal active ingredient is glufosinate-ammonium.

15. The method according to claim 13, wherein the treatment is a foliar application.

16. The method according to claim 13, wherein a total amount of sucrose obtainable from a plant of the genus *Saccharum officinarum* and/or hybrids thereof is increased.

\* \* \* \* \*